(12) United States Patent
Lauer

(10) Patent No.: US 10,507,277 B2
(45) Date of Patent: Dec. 17, 2019

(54) BLOOD TREATMENT CASSETTE WITH FILM VALVE AND ELASTIC SPACER AS WELL AS BLOOD TREATMENT APPARATUS

(71) Applicant: FRESENIUS MEDICAL CARE DEUTSCHLAND GMBH, Bad Homburg (DE)

(72) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 260 days.

(21) Appl. No.: 15/126,253

(22) PCT Filed: Mar. 13, 2015

(86) PCT No.: PCT/EP2015/055281
§ 371 (c)(1),
(2) Date: Sep. 14, 2016

(87) PCT Pub. No.: WO2015/136068
PCT Pub. Date: Sep. 17, 2015

(65) Prior Publication Data
US 2017/0080141 A1    Mar. 23, 2017

(30) Foreign Application Priority Data
Mar. 14, 2014    (DE) .......................... 10 2014 103 490

(51) Int. Cl.
*A61M 1/30* (2006.01)
*A61M 1/16* (2006.01)
*A61M 1/26* (2006.01)
*A61M 1/36* (2006.01)
(Continued)

(52) U.S. Cl.
CPC .............. *A61M 1/301* (2014.02); *A61M 1/16* (2013.01); *A61M 1/1621* (2014.02);
(Continued)

(58) Field of Classification Search
CPC .... A61M 1/301; A61M 1/1621; A61M 1/267; A61M 1/16; A61M 1/3672; A61M 39/22; A61M 2205/128; F16K 7/12
See application file for complete search history.

(56) References Cited

U.S. PATENT DOCUMENTS

2008/0077068 A1* 3/2008 Orr .......................... F04B 7/02
604/6.11
2010/0274168 A1 10/2010 Gronau et al.
(Continued)

FOREIGN PATENT DOCUMENTS

| CN | 102497895 | 6/2012 |
|---|---|---|
| DE | 10-2009-012632 | 9/2010 |

(Continued)

OTHER PUBLICATIONS

International Search Report from PCT/EP2015/055281, dated May 11, 2015.
(Continued)

*Primary Examiner* — Ariana Zimbouski
(74) *Attorney, Agent, or Firm* — Fish & Richardson P.C.

(57) ABSTRACT

A blood treatment cassette having a cassette body comprising a hard part and a film that at least partially covers the hard part. The hard part comprises a valve base that cooperates with a section of the film adjacent the valve base to form a valve that is configured to be moved from a first open position in which the valve base and the section of the film do not touch each other to a second position in which the valve base and the section of the film touch each other when a force is applied to the section of the film. The blood treatment cassette comprises a spacer supported by the hard part, and the spacer is configured to apply, in the first position of the valve, force to the section of the film.

17 Claims, 7 Drawing Sheets

(51) Int. Cl.
*A61M 39/22* (2006.01)
*F16K 7/12* (2006.01)

(52) U.S. Cl.
CPC .......... *A61M 1/267* (2014.02); *A61M 1/3672* (2013.01); *A61M 39/22* (2013.01); *F16K 7/12* (2013.01); *A61M 2205/128* (2013.01); *A61M 2205/273* (2013.01); *A61M 2205/3337* (2013.01); *A61M 2205/3344* (2013.01); *A61M 2206/20* (2013.01)

(56) References Cited

U.S. PATENT DOCUMENTS

| | | | |
|---|---|---|---|
| 2011/0015610 A1* | 1/2011 | Plahey | A61M 1/28 604/500 |
| 2012/0080437 A1 | 4/2012 | Guenther et al. | |
| 2013/0331774 A1 | 12/2013 | Farrell et al. | |

FOREIGN PATENT DOCUMENTS

| | | |
|---|---|---|
| JP | 2005-527303 | 9/2005 |
| JP | 2012-524563 | 10/2012 |
| JP | 2012-533357 | 12/2012 |
| WO | WO 03/099353 | 12/2003 |
| WO | 2014035471 | 3/2014 |

OTHER PUBLICATIONS

International Preliminary Report on Patentability in Application No. PCT/EP2015/055281, dated Sep. 14, 2016, 6 pages (English Translation).

\* cited by examiner

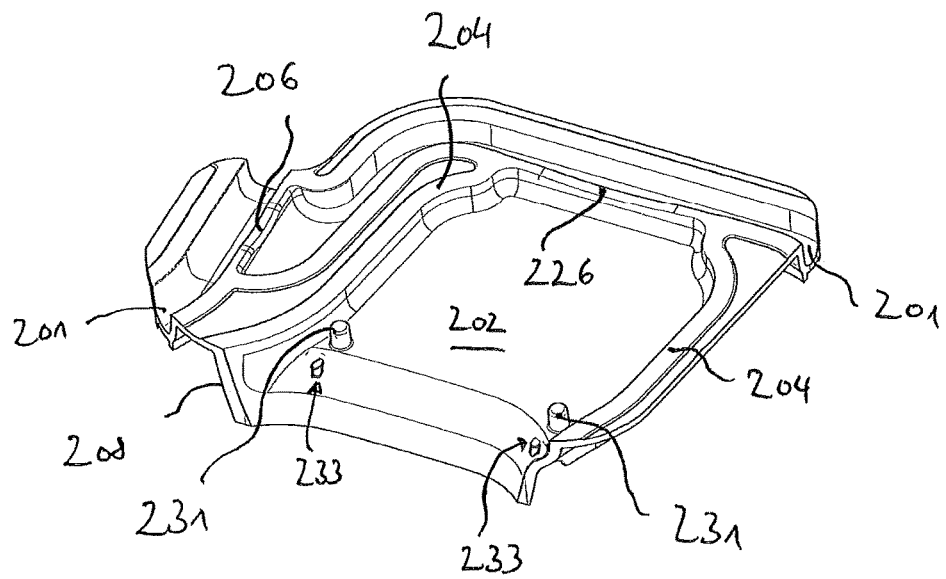
Fig. 4
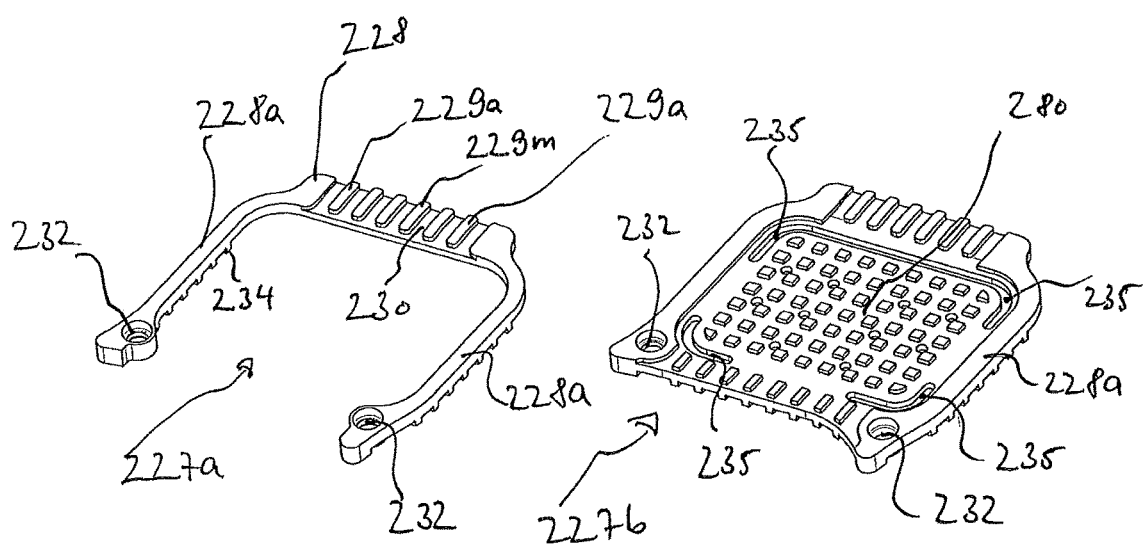
Fig. 5a
Fig. 5b

BLOOD TREATMENT CASSETTE WITH FILM VALVE AND ELASTIC SPACER AS WELL AS BLOOD TREATMENT APPARATUS

CROSS REFERENCE TO RELATED APPLICATIONS

The present application is the national stage entry of International Patent Application No. PCT/EP2015/055281, filed on Mar. 13, 2015, and claims priority to Application No. DE 10 2014 103 490.2, filed in the Federal Republic of Germany on Mar. 14, 2014, the disclosures of which are expressly incorporated herein in its entirety by reference thereto.

TECHNICAL FIELD

The present invention relates to a blood treatment cassette and a blood treatment apparatus.

BACKGROUND

Single-use systems are being increasingly realized in the medical or laboratory technology as compact medical functional devices such as cassette systems or blood treatment cassettes in which liquids and gases, in particular medical fluids and blood, are conducted in channels and chambers. If they are provided for a single use, one speaks of disposable cassettes or single-use cassettes.

In most cases, these are hard-part film cassettes. The hard part regularly consists of an injection molding material such as PE, PP, PA, ABS, PMMA, PC or PVC. In it, for example, hose connections, connectors, chambers, channels and alignment devices are embodied. The chambers and channels are usually designed as semi-open, fluid-conducting structures. A film made of material compatible to the hard part (suitable for welding or gluing to the hard part) seals the semi-open structures and completes them to fully adequate chambers and channels. The film may only be, for example, welded or glued to the blood treatment cassette at an outer complete or closed or peripheral edge. There also are designs where the boundaries of the chambers and channels, the so-called channel edge bars are welded on or glued to the film in strip form or over a larger area. In this manner, blood treatment cassettes which already provide a defined fluid conduction prior to assembling in a treatment machine and after the removal are produced.

Certain areas of the hard part and the film are often deliberately not welded or glued to each other. These areas may be used as film valves between different fluid conducting areas. For this purpose, the blood treatment cassette is inserted in the blood treatment apparatus between a door and an actuator-sensor-unit of the blood treatment apparatus, and subsequently by closing the door, the latter is brought into a so-called grouting or pressing position in which the film is grouted or pressed against the hard part, and the blood treatment cassette with the film is coupled in a spatially defined manner to the actuator-sensor-mat of the actuator-sensor-unit. Actuators integrated into the actuator-sensor-mat and actuator-sensor-plate (or unit) may be able to exercise movements through the film, by which, for example, pump or valve functions may be realized. Properties of fluids which flow through the blood treatment cassette may be measured by means of at least one sensor optionally provided on the actuator-sensor-plate.

Production or processing problems may, however occur, particularly at blood treatment cassettes in which the films and film valves are welded in such a way that they are flush with the channel edge along the latter.

SUMMARY

Aspects of the invention relate to blood treatment cassettes and to blood treatment apparatuses for use with the blood treatment cassettes.

In one aspect of the invention, a blood treatment cassette includes a cassette body designed as hard part as well as a film. The film is connected to the hard part, e.g. through welding or gluing, and the hard part is at least partially covered by the film against the outside such that channels and chambers or parts thereof, are formed by the hard part and the film. Furthermore, the hard part comprises at least one valve seat or section of a valve, herein also denoted as a valve base of the valve.

The valve is designed to take a first position and a second position, or valve position, which is different from the first one. Thereby the first position is a position in which the valve is open, in particular for the gas sterilization of sections of the hard part. In the first position, the valve base and a section of the film, which during the use of the treatment cassette is or will be positioned above the valve base, do not touch each other. The valve is configured and provided in a way that it moves or transitions into the second, closed position when a force is applied, in particular a force directed towards the valve base and acting on the section of the film on top of the valve base. In the second position, the valve base and the section of the film touch each other, for example directly or indirectly. In the second position, the valve is closed.

In addition, the blood treatment cassette and specially the hard part comprise at least one spacer, arranged in particular beneath the film. The spacer is supported resiliently and/or elastically at the hard part and/or it is produced as an integrated part thereof. The spacer is positioned in order to apply, in the first position—and optionally also in the second position—tension, force or pressure on the section of the film arranged above the valve base.

Further, a blood treatment apparatus according to certain aspects of the invention is connected with a blood treatment cassette and comprises an actuator-sensor-plate. The actuator-sensor-plate comprises at least one actuator which comprises at least two, preferably more than three, part-actuators. These are arranged in such a way that they exert force—preferably completely or essentially—independently from each other on the section of the film of the valve.

In all of the following embodiments, the use of the expressions "may be" or "may have" etc., is to be understood synonymously with "preferably is" or "preferably has", respectively, and so on, and is intended to illustrate exemplary embodiments of the invention.

Whenever a numerical word is mentioned herein, the skilled person understands this as an indication of a numerical lower limit. Provided it does not lead to any contradiction discernible for the skilled person, the skilled person in these cases implicitly understands for example "one" always as "at least one". This understanding is also encompassed by the present invention as well as the interpretation that a numeric word, for example, "one" can alternatively be meant as "exactly one", wherever this is technically possible in the view of the skilled person. Both are encompassed by the present invention and apply to all used numerical words herein.

The herein given spatial information such as "top", "bottom", etc. refer, in case of doubt, to the illustrations shown in the here enclosed figures.

Embodiments may comprise one or more of the following features in any arbitrary combination.

In some exemplary embodiments, the valve body and the section of the film arranged above it do not touch each other, neither directly nor indirectly, in an open position of the valve.

In specific exemplary embodiments, the valve is designed to be transferable or to be transferred from the first position into the second position by means of pressure application of an actuator of a blood treatment apparatus on the valve, for the operation of which the blood treatment cassette is connected correspondingly with the blood treatment apparatus.

In certain exemplary embodiments, the valve is designed as a film or a phantom valve.

In some exemplary embodiments, the spacer is an integral part of a spring element connected to the hard part or arranged at it.

In specific exemplary embodiments, the spring element is designed as spring clamp or comprises one.

In some exemplary embodiments of the blood treatment cassette, the spacer is the spring element or the hereinafter described humps.

In certain exemplary embodiments, the spring element comprises at least one fixing opening or bore. The latter is provided to fix the spring element, in a detachable or non-detachable manner, to the hard part by at least one fixing pin pluggable into the at least one bore. In these or in other exemplary embodiments, the spring element comprises at least one fixing pin provided to fix the spring element in at least one fixing opening or bore of the hard part-in a detachable or non-detachable manner.

In some particular exemplary embodiments, the spring element comprises at least two spacers which comprise at least one drainage groove or deepening between the spacers.

In specific exemplary embodiments, the spring element comprises, preferably in its middle range, a function element, preferably a hydrophobic membrane-support grid, a clot trap pad and/or a check valve.

In certain exemplary embodiments, at least a split or split section or a groove is provided between the spring element and the function element. This allows an at least minor relative movement between on the one hand a frame section or spring clamp of the spring element and on the other hand the support grid. Due to that, a mutual interference is hereby advantageously prevented.

In some particular exemplary embodiments, a lowering of the valve base having the shape of a notch, dent or likewise, measured in relation to the adjacent level of the chamber or channel edge bar, here also denoted as dent depth of the valve base, corresponds to 1 to 3 times of the thickness of the film. Alternatively, the valve base may be reset behind adjacent channel edge bars towards the interior of the blood treatment cassette by 1 to 3 times of the thickness of the film.

In specific exemplary embodiments, the spacer comprises a curved top edge with regard to the direction towards the valve base. In some exemplary embodiments, its curvature corresponds to 1 to 4 times of the thickness of the film in the aforementioned direction.

In certain exemplary embodiments, the valve base does not comprise any undercuts.

The film valves described herein are also referred to as phantom valves in connection with the present invention, as, in a closed status with respect to the concerned channels, they do not constitute any change of the flow area compared to channel points or chambers without film valves. They are not identified with regard to the flow area—like a phantom.

In certain exemplary embodiments, the spacer, also denoted herein as spacing device, comprises humps which locally buckle the section of the film lying above them through direct or indirect contact with the latter. In this manner, they create a space between the concerned film section and an adjacent channel bar or the valve base. Thereby, in some exemplary embodiments, the humps protrude over the standard level of the flat film, i.e. over that level in which the film is essentially lying flat on the hard part, e.g. above the gluing or welding level. This may advantageously create a safety distance which allows a reliable flow through the valve being held open.

In some particular exemplary embodiments, the humps of the spacer are arranged to keep the film locally at the standard level of the flat film. Due to the fact that humps or the spacer do not lift the film in the area of the valve beyond the standard level, an unwanted and possibly irreversible stretching of the film section may hereby be advantageously prevented.

In certain exemplary embodiments, the humps are arranged at or on the spacer in a springy and/or flexible manner.

In some particular exemplary embodiments, the spacer comprises, in addition to the humps, a further function element contained in the blood treatment cassette.

In certain exemplary embodiments, the humps (also denoted as elevations) of the spacer are arranged in at least one row parallel to the course of the sealing seat-bar or valve base. With regard to the technical flow, this arrangement may advantageously even keep enough distance between the film and the sealing bar or the valve base if the humps are designed to be only slightly above the channel edge bars with which the film is connected. The flow cross-section is created or determined by the length of the outlet between the valve base and the film generated by the spacer.

In certain exemplary embodiments, the humps are furnished or provided with drainage structures between and/or on the humps. The latter reduce a contact area between the spacer and film during the sterilization and may therefore advantageously contribute to an increased effectiveness of the sterilization process.

In some exemplary embodiments, the humps are positioned at or on one or more spring elements.

In certain exemplary embodiments, the spacer comprises humps which limit the spring path towards the hard part. In this way, as an advantage, an overstress of the spring element may be avoided. As an example, these humps or elevations may be arranged at a bottom side or side surface of the spring element. They may serve as stops or for their part as spacer (for the spring element, not for the film).

In some exemplary embodiments, the spacer is placed in order to ensure a space between the film section and the valve base which allows a gas or vapor exchange across the valve, i.e. between film and valve base.

In certain exemplary embodiments, the spacer impacts on the film from an interior of the blood treatment cassette, i.e. from a space between hard part and film.

In some exemplary embodiments, the blood treatment apparatus comprises a sub-divided or laminated pressure stamp as the actuator. The sub-division or lamination allows the actuator to respond to the curvatures of the valve base.

In certain exemplary embodiments, the sub-divided or laminated pressure stamp comprises a friction-free bearing arrangement for solid joints and/or a spring support.

In some particular exemplary embodiments, the blood treatment apparatus comprises other tolerance-balance or tolerance-compensation devices in the actuator-sensor-unit instead of or supplementary to the laminated pressure stamp with a preferably friction-free bearing arrangement for solid joints and spring support. These include structured or on-the-inner-side-humped actuator-sensor-mats, structured or humped actuator-sensor-plates, inserted foam material and pressure pads, structured interposed elastomer elements and the like.

In some exemplary embodiments, the film valves described herein are those which also perform a function during the use of the blood treatment cassette. In other exemplary embodiments, the film valves only serve as valves with which a flow of sterilization means between chamber and channel/chamber shall be ensured before the use of the blood treatment cassette. In these embodiments, the film valve remains closed by means of the actuator after the beginning of the blood treatment session.

Some or all embodiments may comprise one or more of the above or below mentioned advantages.

During the sterilization of the blood treatment cassette with gas or vapor, usually several changes between vacuum and excess pressure phases take place for the gas exchange. Thereby the sealing seat areas of the valves that are neither welded nor glued act as flow resistances. At the change or switchover from vacuum to excess pressure, they occasionally and unintentionally even act as check valves in case the film becomes deformed towards the cavities and chambers of the blood treatment cassette due to the delayed pressure balance or compensation generated in the blood treatment cassette. Thereby, it is possible that the film valves close and therefore hamper or even prevent sterilization gases to enter into single channels or chambers resulting in a poor or insufficient sterilization. So far, one had to revert to uneconomical sterilization methods to solve this problem. These disadvantages may be reduced or avoided by blood cassettes described herein due to the fact that, thanks to the spacer, its film valves remain open even when negative pressure is applied during the sterilization process.

Mechanical stress occurring due to the transition or change from vacuum to excess pressure and vice versa may be prevented or at least reduced due to the spacer provided. It maintains the pressure on the film above the film valves at which the film is not welded on the hard part. This may counteract a sagging of the films resulting from mechanical stress.

A technical solution is thus proposed by the present invention which advantageously allows the film at one point or at several points of the boundaries of the chambers and channels to be spaced apart from the hard part so that, analogous to the functionality of the phantom valve described already, a fluidic connection builds up between the chambers and the channels. Therewith, the transport of the sterilization gas is improved and the film stress generated due to pressure change is reduced.

A further advantage is the possible tolerance balance or balance compensation which is possible due to the springy positioning of the spacer but also due to the multiple-part or laminated design of the actuator for the closing of the film valve. The actuator of the blood treatment apparatus thereby serves as tolerance-balance or tolerance-compensation device for dented, i.e. not straight film-sealing seat-bars, for which an installation tolerance balance or tolerance compensation and a form tolerance balance or tolerance compensation in the direction alongside the sealing seat bar is ensured for example via independently movable blades.

The actuator-sensor-unit, the tolerance-balance or tolerance-compensation devices may hereby advantageously maintain the sealing effect of flat or dented film valves and are robust against dimensional tolerances of the blood treatment cassette, the blood treatment device or the alignment between blood treatment cassette and blood treatment device.

BRIEF DESCRIPTION OF THE FIGURES

The present invention shall be exemplarily explained in the following by way of the accompanying drawings, in which identical reference numerals designate same or similar elements. In the partially simplified figures:

FIG. 4 shows perspectively a section of a hard part of a blood treatment cassette;

FIGS. 5a,b show perspectively a spring element of the blood treatment cassette;

The standard arrows in the figures indicate the direction of the blood stream. The block arrows indicate the respective direction of the substitute stream.

DETAILED DESCRIPTION

Figure 1:
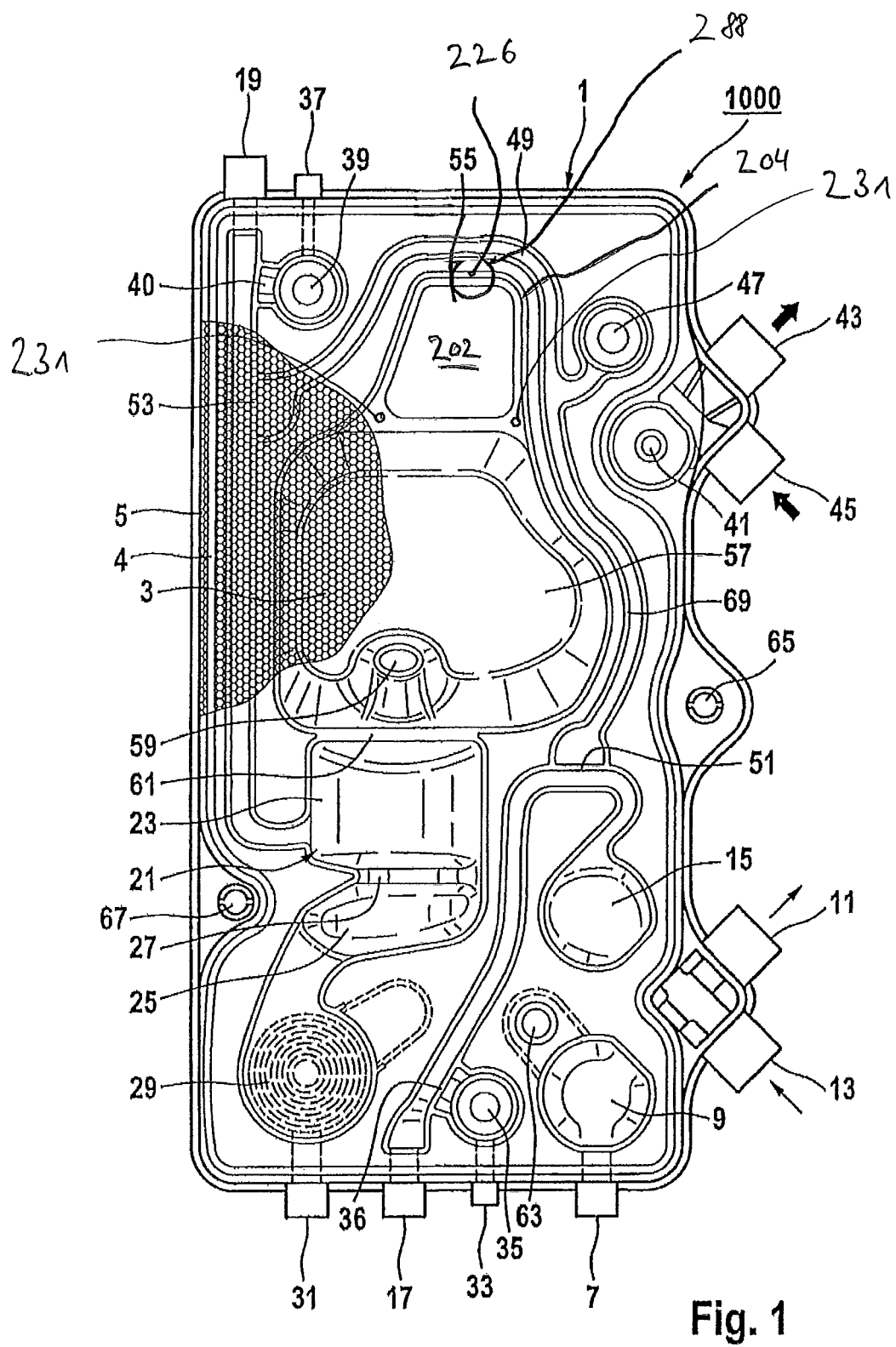
FIG. 1 shows a lateral view of a blood treatment cassette provided in accordance with an embodiment, having a cover on its front side.

FIG. 1 shows a lateral view of a blood treatment cassette 1000 which is provided with a cover device at the surface one looks upon in FIG. 1.

In the following, the blood treatment cassette 1000 is also referred to as cassette 1000 in short.

The cassette 1000 comprises a hard part 1. As it is exemplarily shown in FIG. 1, the hard part 1 comprises chambers, channels and valves. As it is furthermore exemplarily shown in FIG. 1, the chambers, channels and valves are integrated into the hard part 1 or are at least partly formed by the hard part 1.

The cassette 1000 of FIG. 1 is provided at its front side with a cover, here, for example, a film 3. The cover may be welded in a flat manner, i.e., planarly, onto the hard part 1.

An embodiment involving a three-dimensional configuration of the welding and sealing contour is also possible.

The cover device may close the chambers and/or channels of the hard part 1 of the cassette 1000, namely, against a side of the cover means facing away from the hard part 1 and/or against the atmosphere.

As seen in FIG. 1 the film 3 rests on the hard part 1 of the cassette 1000 at a closed sealing bar 4. The film 3 is welded to or on the hard part 1 of the cassette 1000 at a closed weld 5.

The closed sealing bar 4 may alternatively be realized in an exposed manner.

The film 3 may be connected to the hard part 1 of the cassette 1000 at additional local welds (not shown). These may also be closed or peripheral, i.e. closed in the sense of an enclosing limitation similar to a ring, and/or dot-shaped.

The film 3 may locally be connected, e.g. welded, to the hard part 1 of the cassette 1000 in form of dots or a line, in particular at the edge zones of the liquid-conducting channels.

The film 3 may be connected to the hard part 1 of the cassette 1000 by laser welding. If so, it is advantageous if the heat is locally applied while using a light-absorbing component. The light-absorbing component may be part of the material of the film 3 and/or of the hard part 1, or a layer disposed between film 3 and hard part 1 or above the film 3. The layer may be a film layer.

The cassette 1000 may at least be coupled with a blood treatment apparatus (not shown in FIG. 1) at its front side shown in FIG. 1. An exemplary technique for suitable coupling of a cassette 1000 to a coupling surface of a blood treatment apparatus is described in the patent applications 10 2009 012 633.3 having the title "Vorrichtung zum Verbinden einer externen Funktionseinrichtung mit einer Anordnung, Anordnung aufweisend eine solche Vorrichtung und Verfahren zum Verbinden" [Device for connecting an external functional means to an arrangement, arrangement including a like apparatus, and connecting method] as filed with the German Patent and Trademark Office on Mar. 10, 2009, and 10 2009 012 632.5 having the title "Abdichtungseinrichtung zum Abdichten eines Volumens einer medizinischen Behandlungsanordnung gegen ein weiteres Volumen sowie Anordnung und Verfahren" [Sealing means for sealing a volume of a medical treatment arrangement against another volume, as well as arrangement and method] also filed with the German Patent and Trademark Office on Mar. 10, 2009, the respective disclosures of which are herewith fully incorporated by way of reference.

The cassette 1000 may be coupled with a coupling surface of the blood treatment apparatus by the plane of the film 3 or through the intermediary of the latter. The coupling area may preferably be executed three-dimensionally.

The coupling surface of the blood treatment apparatus may be inclined to the rear, for instance at an upper portion thereof shown in FIG. 1, by 8 degrees against a vertical line extending from top to bottom in FIG. 1 (in the direction extending from the observer into the plane of drawing in FIG. 1).

The cassette 1000 comprises an arterial patient connection 7.

The cassette 1000 comprises an arterial pressure measurement chamber 9. The latter may include corresponding sensors. The sensors may transmit signals, preferably through the intermediary of cables or cabling. The sensors may, however, also be provided to transmit signals in a wireless manner.

The cassette 1000 comprises a connector 11 for the exit of blood from the cassette 1000 as well as a connector 13 for the entry of blood into the cassette 1000.

The two connectors 11 and 13 are adapted to be connected to a pump tube segment or pump tube set of a blood pump.

The cassette 1000 further comprises a chamber 15 including a pressure measurement site for pressure measurement in the extracorporeal blood circuit upstream from the dialyzer ("pre-filter") or downstream from the pump ("post-pump"), respectively.

At the chamber 15 the pressure in the extracorporeal circuit upstream from the dialyzer may be measured across the film 3 or via the film 3.

The cassette 1000 comprises an arterial filter conduit 17 as well as a venous filter conduit 19.

The interior of the cassette 1000 comprises a venous blood chamber 21. The venous blood chamber 21 is subdivided into an upper space 23 and a lower space 25.

The upper space 23 of the venous blood chamber 21 may admit a laterally tangential inflow of blood. Here, blood may flow in laterally through the inlet (on the left side in FIG. 1) into the upper space 23 and spread out tangentially to the walls of the upper space 23. A laterally tangential inflow of blood may create a zone with a substantially or completely stable rotational flow of blood in the upper space 23 of the venous blood chamber 21.

The lower space 25 of the venous blood chamber 21 may represent a calming zone for the blood stream. Such a calming zone may possibly have substantially no rotational flow or no rotational flow of the blood present therein at all.

The venous blood chamber 21 is subdivided into the upper space 23 and the lower space 25 by a cross-sectional restriction 27 of the hard part 1 of the cassette 1000. The cross-sectional restriction 27 reduces the cross-section of the venous blood chamber 21 in its width and depth so as to result in a shoot or rapid, whereby a fluid having traversed the cross-sectional restriction 27 will flow with slower flow velocity through venous blood chamber 21 of the cassette 1000. The upper space 23 and the lower space 25 are in fluid communication.

By using such a construction, i.e., a subdivision of the venous blood chamber 21 into a zone with substantially or completely stable rotational flow of the blood and a calming zone for the blood stream, it is advantageously possible to achieve an efficient separation of air from the blood or fluid.

Walls of the upper space 23 and of the lower space 25 of the venous blood chamber 21 may suitably be adapted to an inclination from the vertical position of the upper portion of the cassette 1000 in FIG. 1, for example an inclination to the rear by 8 degrees (into the plane of the drawing) of the upper part of the cassette 1000 shown in FIG. 1. They may suitably have a rounded shape in a way that they advantageously represent a flow-optimized contact surface for fluids passing through the venous blood chamber 21.

The cassette 1000 comprises a clot trap 29.

The clot trap is preferably a clot trap as disclosed in the patent application (10 2009 024 495.6) having the title "Gerinnselfänger, externe Funktionseinrichtung, Blutkreislauf sowie Behandlungsvorrichtung" [Clot trap, external functional means, blood circuit and treatment apparatus] to the applicant of the present invention that was filed with the German Patent and Trademark Office on Jun. 10, 2009. The relevant disclosure thereof is herewith fully incorporated by way of reference.

At the clot trap 29 it is possible to measure the pressure in the extracorporeal circuit through the film 3 or across the film 3, i.e., in particular after passage through the dialyzer or downstream of the dialyzer.

The cassette 1000 comprises a venous patient connection 31.

The cassette 1000 comprises an arterial heparin addition site 33. Here, it should be noted that the heparin addition site 33 (just like a venous heparin addition site 37) may also be suited and intended for adding other pharmacologically effective agents than heparin, which are only in a preferred manner anti-coagulants or combinations of active agents. This should also be noted whenever heparin is mentioned previously or in the following in any kind of context.

The cassette 1000 comprises a check valve 35 at the arterial heparin addition site 33.

Exemplary check valves for the use as check valve 35 of the arterial heparin addition site 33 and also as further check valves of the cassette 1000 are disclosed in the patent application to the applicant of the present invention (10 2009 024 469.7) having the title "Ventilvorrichtung, Ventileinsatz, externe Funktionseinrichtung, Behandlungsvorrichtung sowie Verfahren" [Valve device, valve insert, external functional means, treatment apparatus, and method] as filed with the German Patent and Trademark Office on Jun. 10, 2009, the relevant disclosure of which is herewith fully incorporated by way of reference.

The cassette 1000 comprises an arterial heparin addition valve 36. By using the arterial heparin addition valve 36 the addition of heparin into the arterial filter conduit 17 may be controlled or regulated.

The arterial heparin addition valve 36 may be configured as a so-called phantom valve.

The expression "phantom valve" as used herein designates an element having an actor surface (in the present case, for example, an actor membrane) that may be reached by an actor that may adopt the function of a valve.

The actor membrane can be made to move, dilate, curve, etc. in one direction by applying a force on it, e.g., a pressing force. As a result of its movement or dilatation, the actor membrane may come into contact with an element such as a sealing device, e.g. a bar, or move away from the latter. The actor membrane may thus, for example, effect or enhance or terminate or reduce a sealing effect.

When the force acting on the actor membrane is ceased to apply or is released, the latter may return, for example, to a basic position, e.g., a non-bent condition.

A phantom valve for use as an arterial heparin addition valve 36 as well as further phantom valves of the cassette 1000 may be configured with or from a bar portion of a channel at the hard part 1 of the cassette 1000 and a portion of the film 3 contacting or facing the bar portion.

Phantom valves may be operated through actors of the blood treatment apparatus.

In order to close a phantom valve, the portion of the film 3 may be pressed onto the bar portion. In order to open the phantom valve, the portion of the film 3 may again be raised or removed from the bar portion.

Further examples of phantom valves may be found in the patent application 10 2009 012 632.5 having the title "Abdichtungseinrichtung zum Abdichten eines Volumens einer medizinischen Behandlungsanordnung gegen ein weiteres Volumen sowie Anordnung und Verfahren" [Sealing device for sealing a volume of a medical treatment arrangement against another volume, as well as arrangement and method], as filed with the German Patent and Trademark Office on Mar. 10, 2009 by the present applicant besides the patent application DE 100 53 441 A1 and the patent application DE 102 24 750 A1. The relevant disclosures thereof are herewith fully incorporated by way of reference.

The cassette 1000 comprises a venous heparin addition site 37. The venous heparin addition site 37 may be configured as a Luer-connector.

The cassette 1000 comprises a check valve 39 at the venous heparin addition site 37.

The cassette 1000 comprises a venous heparin addition valve 40. With the aid of the venous heparin addition valve 40 the addition of heparin into the venous filter conduit 19 may be controlled or regulated.

The cassette 1000 comprises a substituate addition site 41 or a substituate connector, respectively.

The substituate addition site 41 may be a connection means as it is described in the patent application 10 2009 024 575.8 to the present applicant having the title "Verbindungseinrichtung und Verfahren zum Verbinden wenigstens zweier fluidführender medizintechnischer Systeme, sowie medizintechnische Vorrichtung" [Connection means and method for connecting at least two fluid-conducting medical-technical systems, as well as a medical-technical apparatus] as filed with the German Patent and Trademark Office on Jun. 10, 2009 by the present applicant. The relevant disclosure thereof is herewith fully incorporated by way of reference.

The substituate addition site 41 may be provided with a touch-protection element (not shown). The substituate addition site 41 may be provided with a drip-protection element (not shown). The drip-protection element may be realized through an integrated closure sleeve. The drip-protection element may prevent residues of substituate and/or blood from dripping out when the cassette 1000 is released and subsequently removed from the blood treatment apparatus.

The drip-protection element may be realized to be removable. It may be configured as a hood or lid.

The substituate addition site 41 or some other portion of the cassette 1000 may moreover provide a tamper protection, as a result of which the user recognizes effortlessly, or at one glance, whether the cassette 1000 has already been used. This tamper protection may be realized by means of the touch-protection element, the closure sleeve, or some other structure. Preferably, the corresponding structure may recognizably change its position inside or relative to the cassette 1000. Preferably it may change its shape.

Moreover, the substituate addition site 41 or some other portion of the cassette 1000 may provide a protection against reuse. In a preferred manner, the cassette 1000 is made unusable by means of a closure sleeve—preferably in an irreversible manner—with respect to an attempted reuse. If the cassette 1000 should nevertheless be used again, sensors of the blood treatment apparatus do not measure the signal characteristics that would be measured during use of a new cassette. This may be due to the fact that liquid cannot enter into the cassette 1000 or into the substituate addition site 41, or at least not in a sufficient or usual quantity. The control unit of the blood treatment apparatus may recognize this. A warning may be triggered.

As a tamper protection or a protection against reuse it is preferably possible to use a tamper protection or protection against reuse as disclosed by the applicant of the present invention in the patent application (10 2009 024 575.8) having the title "Verbindungseinrichtung und Verfahren zum Verbinden wenigstens zweier fluidführender medizintechnischer Systeme, sowie medizintechnische Vorrichtung" [Connection means and method for connecting at least two fluid-conducting medical-technical systems, as well as a medical-technical apparatus] that was filed with the German Patent and Trademark Office on Jun. 10, 2009. The relevant disclosure thereof is herewith fully incorporated by way of reference.

The cassette comprises a connector 43 for the exit of substitute from the cassette 1000 as well as a connector 45 for the entry of substitute into the cassette 1000.

The connectors 43 and 45 are adapted to be connected to a pump tube segment or a pump tube set of a substitute pump.

The cassette 1000 comprises a check valve 47 for the addition of substitute.

Substitute may be introduced into a substitute conduit 49 by operating the check valve 47.

The cassette 1000 comprises a pre-dilution addition valve 51. The pre-dilution addition valve 51 may be configured as a phantom valve.

The cassette 1000 comprises a post-dilution addition valve 53. The post-dilution addition valve 53 may be configured as a phantom valve.

The cassette 1000 comprises a single-needle sterile membrane 55.

The cassette 1000 comprises a single-needle chamber 57. In FIG. 1, the single-needle chamber 57 is disposed above the venous blood chamber 21.

Inside the single-needle chamber 57 a blood surge redirection element 59 is arranged. The blood surge redirection element 59 may serve for decelerating a blood surge and/or extinguishing its impulse.

A connection to an inside of the single-needle chamber 57 may be provided by means of connection means as disclosed by the applicant of the present invention in the patent application (10 2009 024 467.0) having the title "Einrichtung sowie externe Funktionseinrichtung und Behandlungsvorrichtung zum Behandeln von medizinischen Fluiden" [Device and external functional means and treatment apparatus for the treatment of medical fluids] that was filed with the German Patent and Trademark Office on Jun. 10, 2009. The relevant disclosure thereof is herewith fully incorporated by way of reference.

The cassette 1000 comprises a single-needle blood valve 61. The single-needle blood valve 61 may be configured as a phantom valve.

The cassette 1000 comprises an evacuation site 63. The evacuation site 63 may serve for vacuum coupling of the cassette 1000 to the blood treatment apparatus as is described, for example, in the patent application DE 10 2007 042 964 A1 having the title "Vorrichtung und Verfahren zur Behandlung einer medizinischen Flüssigkeit" [Apparatus and method for treating a medical liquid] that was filed with the German Patent and Trademark Office on 10 Sep. 2007. The relevant disclosure thereof is herewith fully incorporated by way of reference.

The cassette 1000 comprises a primary alignment center 65. The primary alignment center 65 may advantageously serve for aligning and/or latching of the cassette 1000 on the blood treatment apparatus.

The cassette 1000 comprises a secondary alignment site 67. The secondary alignment site 67 may serve for aligning and/or latching of the cassette 1000 on the blood treatment apparatus.

The cassette 1000 is filled with gas (e.g., sterile air) prior to beginning priming. During priming of the extracorporeal blood circuit this gas filling has to be displaced. Insofar, a blood treatment cassette generally represents a particular challenge as there are both rising and falling conduits and moreover chambers in which no air "nests" must remain. For this purpose, the present cassette 1000 is provided with special construction features.

The chamber 15 for measuring the arterial pressure is constructed such that air may rise into a pump tube segment (e.g. into the pump tube segment). Advantageously, there are no dead spaces present. Air rising by itself from the arterial pressure measurement chamber into the pump tube segment of the blood pump is forcibly conveyed through the pump tube segment from the engagement range of the blood pump (e.g., by the rollers of a roller pump). As soon as the pump ceases to exert an influence (for example due to disengaging the rollers), the air rises by itself into the cassette 1000 in the conveying direction.

The venous recirculation conduit (or a venous portion of the extracorporeal circuit) is a downward conduit. Starting from a particular prevailing volume flow (e.g., 200 ml/min in the case of the cassette 1000 shown in FIG. 1), air bubbles in the blood are "entrained" even against gravitational acceleration or gravitation. This effect is made use of in the downward conduits. The conduit cross-sections of the downward conduits are designed with such a small size that a forcible conveyance of the air bubbles even against gravitational acceleration is successful due to the flow velocity.

In the venous blood chamber 21 large cross-sections are provided, such that air bubbles may reliably rise there against the main direction of flow due to the slower or lower flow velocities present in this location.

Further constructive features of the cassette 1000 are as follows:

The phantom valves 40, 51 and 53 are arranged such that blood (which has a higher density than water or substitute etc.) can hardly penetrate "upward" or "sideways" into opened phantom valves while the cassette 1000 is operated with blood, for the latter descends as compared to the lighter water. Such an advantageous orientation is achieved with the aid of the phantom valves 40, 51, and 53. The valve 36, on the other hand, does not imply such a requirement, i.e., the orientation is not crucial there.

For the same reason, the conduit channel (stub channel) below the check valve 47 for adding substitute is constructed or arranged in a rising manner. In the event of a malfunction of the pre- and/or post-dilution valves 51 and 53 and a resulting bypass flow of blood, blood cannot rise into the substitute conduit 49 anymore. The blood will rather flow past the opening of the corresponding stub conduit.

The inclination of the cassette 1000 preferably is from 5 degrees to 11 degrees, in a particularly preferred manner it assumes the 8 degrees already mentioned above.

Reference numeral 288 denotes a phantom valve which allows in the first position a flow in the chamber 202 or prevents it in a second position. In its simplest embodiment, a phantom valve is a film valve through which a fluid path, between hard part 1 and the section of the film disposed above it, is prevented through temporary pressing of the film 2 on a valve base, like a bar or other sections of the hard part 1, and reopened after release of the pressing force.

The reference numeral 202, 204, 226 and 231 are elucidated in the description of FIGS. 4 to 12.

Figure 2:
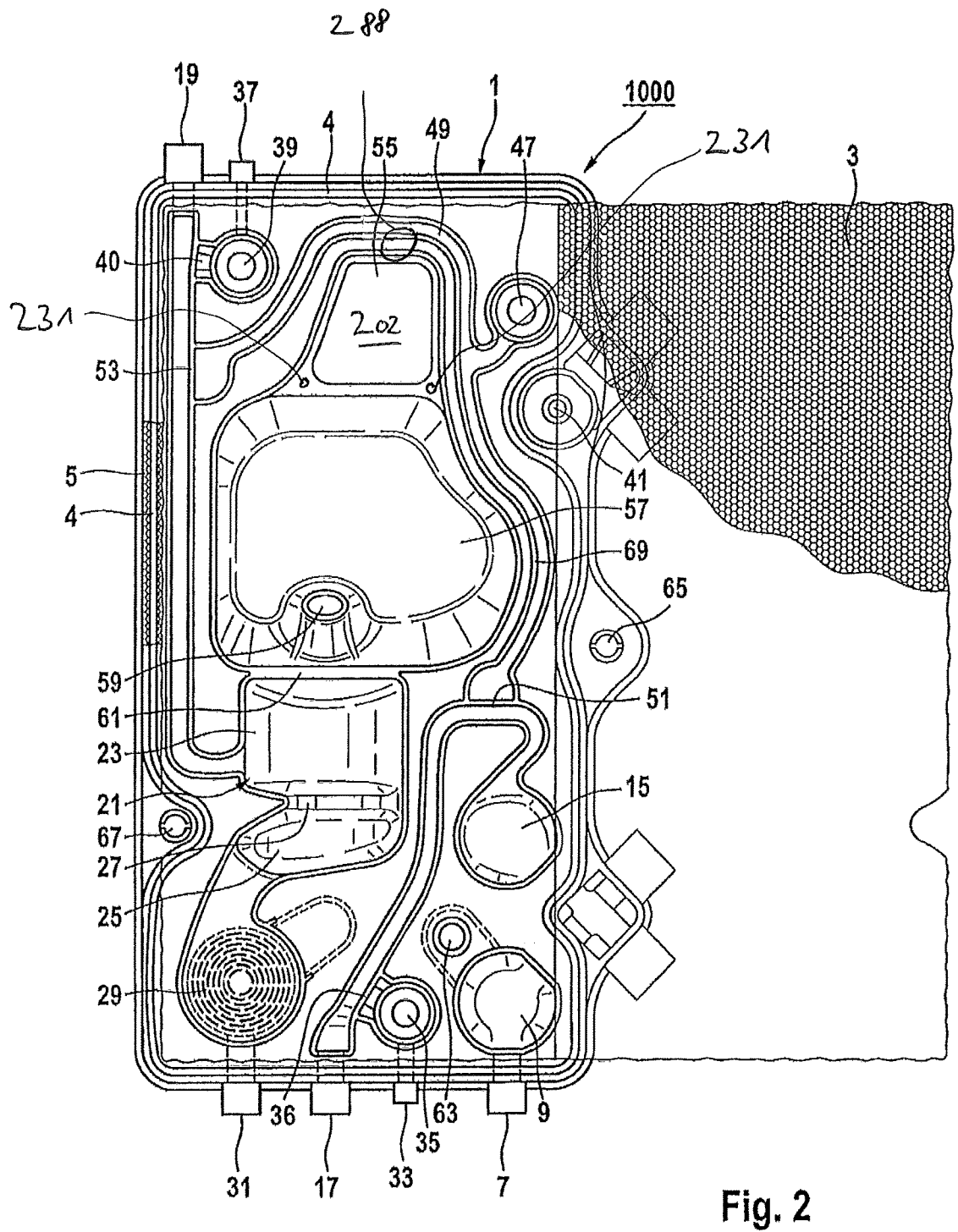
FIG. 2 shows the external functional device of FIG. 1 with the cover means swung-open following destructive cutting.

FIG. 2 shows the cassette 1000 of FIG. 1, wherein the film 3 is recognized to be cut open destructively at the left-hand margin of the cassette 1000 as well as at the top and bottom and swung open to the right for better illustration.

As is shown in FIG. 2, the film 3 comprises a surface texture. FIG. 2 shows the elements inside the cassette 1000 which are visible in more detail after having cut open the film 3. In order to avoid repetitions, reference is made to the configurations of the aforesaid individual elements discussed in the description of FIG. 1.

Here, it is clearly seen that the cassette 1000 comprises a sealing bar 69. The sealing bar 69 may be employed, for example, for realizing the pre-dilution addition valve 51.

Figure 3:
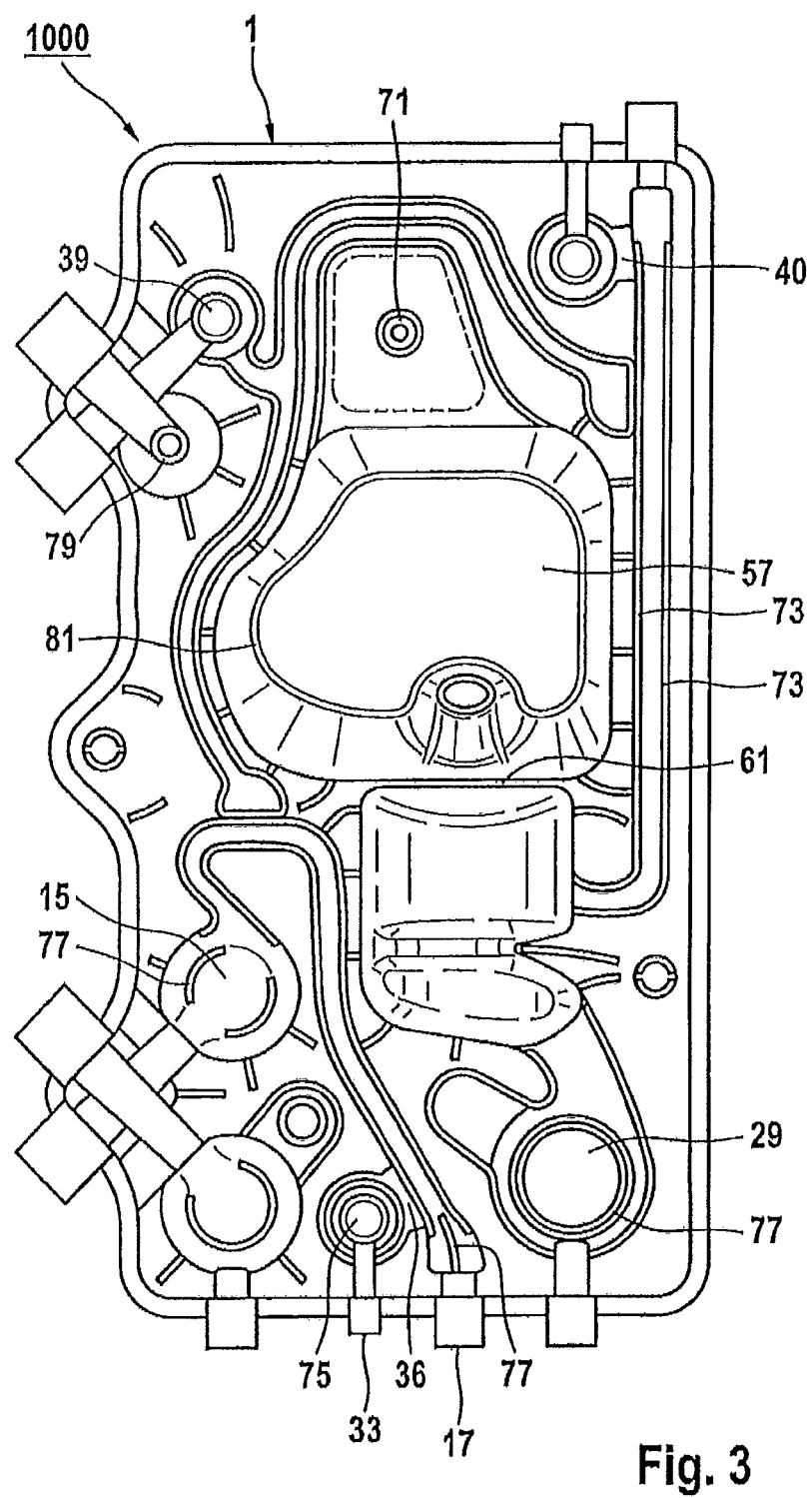
FIG. 3 shows the blood treatment cassette of FIG. 1 and FIG. 2 from its rear side.

FIG. 3 shows the cassette 1000 from its rear side. When the cassette 1000 is coupled with the blood treatment apparatus, an observer opening a door of the blood treatment apparatus for removing the cassette 1000 will look upon this rear side.

The cassette 1000 comprises a single-needle air connector 71. It may be provided to arrange a support grid (not shown) of the single-needle sterile membrane 55 at the single-needle air connector 71 on the apparatus side and/or on the blood side.

The cassette 1000 comprises several support bars. The support bars have different heights relative, e.g., to the plane of the film 3. The support bars are projected in the side of the cassette 1000 facing the observer in FIG. 3, i.e., out of the plane of drawing of FIG. 3.

The cassette 1000 comprises support bars 73 having a height of 5 mm, support bars 75 having a height of 8 mm, support bars 77 having a height of 13 mm, support bars 79 having a height of 24 mm, and support bars 81 having a height of 31 mm. These and other numeric values should, of course, be understood as mere examples.

The support bars may serve to support the cassette, in the state of being coupled to a blood treatment apparatus, against a lid of a reception portion of the blood treatment apparatus for receiving the cassette. Exemplary embodiments of such a coupling of the cassette to the blood treatment apparatus are given in the patent application 10 2009 012 633.3 having the title "Vorrichtung zum Verbinden einer externen Funktionseinrichtung mit einer Anordnung, Anordnung aufweisend eine solche Vorrichtung and Verfahren zum Verbinden" [Device for connecting an external functional means to an arrangement, arrangement including a like apparatus, and connecting method] as filed with the German Patent and Trademark Office on Mar. 10, 2009, the relevant disclosure of which is herewith fully incorporated by way of reference.

In FIG. 3 the cassette 1000 is shown as it will be viewed by the user/observer after its coupling to the machine interface. The inclination of the cassette 1000 relative to the machine is realized with a 'rearward inclination', so that the upper edge is located at a further distance from the user/observer than the lower edge.

The upwardly-facing surfaces of the venous blood chamber 21 and of the single-needle chamber 57 accordingly comprise such an inclination that air bubbles may still reliably rise on the inside despite the inclination of the cassette 1000. As an alternative, a cassette design which does not provide any inclination of the cassette is, of course, basically also possible.

The following figures show sections of a cassette 1000 which may by all features be in accordance with the cassette 1000 of FIGS. 1 to 3, as long as it does not deviate in the following described embodiments therefrom. In any case, the cassette 1000 of the following figures may comprise features of the cassette 1000 shown in FIG. 1 to FIG. 3 as long as the respective features combinations is not realized by the skilled person to be technically impossible.

FIG. 4 shows, perspectively, a section of a hard part 1 of a cassette 1000, for example the one of the aforementioned figures. The hard part has channels 201, a chamber 202, closed, flat channel edge bars 204 at which the film 3 is glued to or welded on the hard part 1. Furthermore, a section 226 of the hard part 1, realized as dented, is illustrated which continues into the channel edge bar 204 or interrupts it. The film 3 is not glued to or welded on the section 226 of the hard part disposed beneath it, thus enabling the valve effect mentioned supra. The section 226 is herein denoted as film as a film-sealing seat-bar 226. Instead of the dented configuration as shown in FIG. 4, the section 226 may also be flat or straight.

FIG. 4 further shows two fixing pins 231, by means of which a spring element 227a or 227b, as shown in the FIG. 5a or 5b, may be connected to the hard part 1. Support humps 233 which are provided in the area of the fixing pins 231 are described further below.

FIGS. 5a and 5b show, perspectively, a spring element 227a or 227b of the cassette 1000, herein also denoted as disposable spring element. The spring element 227a is, purely exemplary or substantially, U-shaped and embodied with at least one spring clamp 228 and at least one spring arm 228a. It serves exclusively or primarily to position, in a front area of its spring clamp 228, a number of marginal humps 229a and a number of centrally arranged humps 229m with drainage grooves 230, optionally arranged in-between, and to place them in an elastically flexible manner in a direction perpendicular to the film 3.

In order to fulfil the function of alignment, placing and springing of the humps 229a, 229b, it is preferred that the spring element 227a, 227b is made of similar material as the hard part 1 (e.g. of thermoplast, preferably with a flexural-E-Modulus of circa 800 to 2000 $N/mm^2$).

Due to its favourable shaping, the spring element 227a, 227b may advantageously be produced extremely cost-effective in open/close multi-injection molding tools.

FIG. 5b shows another exemplary embodiment of the spring element 227b, which comprises an integrated hydrophobic membrane-support grid 280. Instead of the hydrophobic membrane-support grid 280—or supplementary hereto—components such as clot trap pads, check valves and so on are provided in or on the spring element 227b. In this way, the function of a spring element may be integrated in an already required component, as those aforementioned, which advantageously leads to the reduction of the extra expenses for achieving the spring element function.

The spring element 227a, 227b is positioned and fixed in the example of FIGS. 5a, 5b by pushing, clipping and/or thermally riveting its fixing bores 232 on the fixing pins 231 of the hard part 1 of the cassette 1000.

Optionally provided support humps 233 of the hard part 1, see FIG. 4, and support ribs 234 which are provided at least on one of the spring arms 228a of the spring element 227a, 227b and preferably at the bottom side of the spring arm 228a, ensure in certain exemplary embodiments of the present invention together with fixing pins 231 which are optionally provided on the sides of both spring arms 228a a free-of-play, three-point placement of the spring element 227a, 227b in the chamber 202 of the cassette 1000. In some embodiments, the support humps 233 limit the height or angle at which the spring element 227a, 227b may lift off, in a front area therefrom with the fixing pins 231 as a pivot point, from the hard part 1 or from the channel edge bars 204.

On the other side of the support ribs 234—i.e. in the direction of the front section or spring clamp 228 of the spring element 227a, 227b—the latter comprises no more support ribs 234. Due to its thin shaping and its secured spacing to the ground and to the walls of the chamber 202, the spring element 227a, 227b may spring freely and elastically.

In the exemplary embodiment of the FIG. 5b, the spring element 227b is mechanically uncoupled from the hydrophobic membrane-support grid 280 by one or more splits 235. The function of the hydrophobic membrane-support grid 280 remains therefore absolutely unaffected by the function and movement of the spring element 227b.

Figure 6:
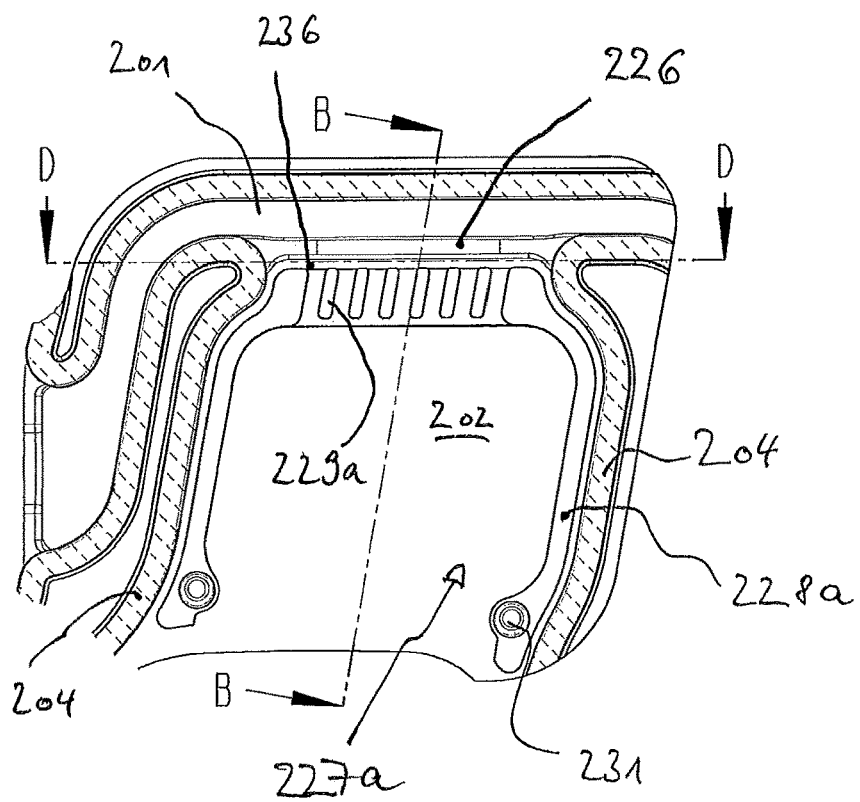
FIG. 6 shows a top view of the section of the blood treatment cassette shown in FIG. 4 having an integrated spring element.

FIG. 6 shows a top view of the section of a cassette 1000 illustrated in FIG. 4 having an integrated spring element 227a of the FIG. 5a and having a transparently illustrated and therefore unrecognizable film 3 which is glued or welded to the channel edge bars 204. The glued or welded channel edge bars 204 have a height at which the straightened film 3 may lie stress-free. Channel edge bars 204 therefore reach up to the film 3 and could substantially be in contact therewith without being glued or welded.

The section 226 encompasses the film valve sealing seat-bar as a valve base of a valve or film valve 288 designed as phantom valve at which the film 3 is not glued to or welded on the section of the hard part 1 disposed underneath it (or at which the section of the hard part 1 arranged above the film 3 is not glued to or welded on the film 3).

The section 226 may be straight (i.e. with a straight upper edge) or dented (i.e. with concave or convex, but in any case dented upper edge). In the purely exemplary dented embodiment which is shown in FIG. 6, the depth of the dent, which is illustratively shown in FIG. 7 in an enlarged view, initially increases from the base of the straight upper edge of the hard part 1 in order to decrease again after reaching a lowest point.

Figure 7:
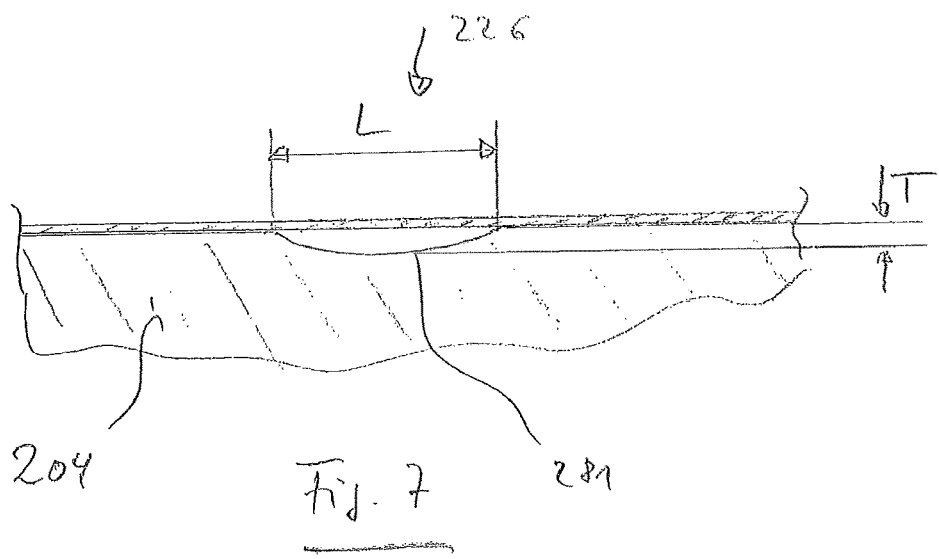
FIG. 7 shows a dent of a valve in the blood treatment cassette.

In the illustrated exemplary case of the FIG. 6, the dented section 226 comprises a particularly low dent-depth T by particularly high dent-width and sealing-seat-bar length L, see also FIG. 7 for a better understanding of the aforementioned dimensions, wherein the non-illustratable dent-width extends into the plane of drawing and the reference numeral 281 denotes the dent-base.

In connection with the low split 235 between the spring element 227a, which preferably corresponds to 2 to 6 times the thickness or strength of the film 3 and due to the high number of humps 229a on the spring element 227a, a large flow cross section connection advantageously is achieved by low dent-depth T of about 1 to 3 times of the film strength between the channel 201 and the chamber 202. By closing the machine door, the cross section connection is closed by a film hub corresponding to only 2 to 4 times of the film strength.

Due to this elastical arrangement of the humps 229a, 229m in addition to the large dimension of the flow cross section, an undesired closing of the valve 288 in the area of the section 226 during the production of the cassette 1000 and up to the completion of the gas sterilization, is particularly effectively prevented. This is also because the spring element 227a, 227b, is designed against overload due to bending technique due to its design and due to its securely embodied path limitation on the ground of the chamber 202 and that the film 3 always lifts up from the dent base 281 even if the film 3 should already have a prior damage in the shape of dents.

Due to the support ribs 234, the free-bending spring arm 228a as well as the humps 229a, 229m having drainage grooves 230 in between, the spring element 227a 227b may have a direct contact with the hard part 1 and with film 3 only at few points whose overall surface is only few square millimeter (mm$^2$). In this way, the gas sterilization of all relevant surfaces is advantageously ensured.

Figure 8:
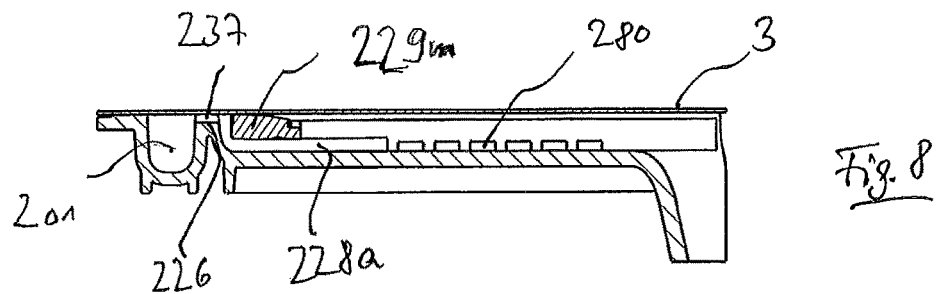
FIG. 8 shows a section or cut through of the not-yet-equipped blood treatment cassette of FIG. 6 along the line B-B in FIG. 6.
Figure 9:
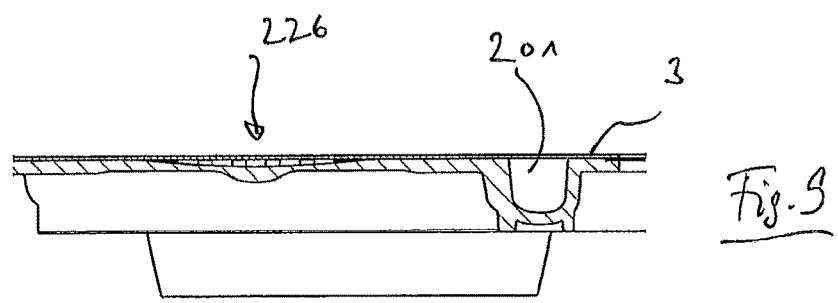
FIG. 9 shows a section or cut through of the not-yet equipped blood treatment cassette of FIG. 6 along the line D-D in FIG. 6.

FIG. 8 and FIG. 9 show cuts through the cassette 1000 of FIG. 6 which is not yet equipped (i.e. not yet connected with the blood treatment apparatus) as cuts along the lines B-B (FIG. 8) or D-D (FIG. 9), each with horizontally lying film 3.

In this embodiment, the section 226 or the film valve-sealing seat-bar or the valve base is bent and comprises humps 229m which do not overtop the level of the film 3.

In FIG. 8, the reference numeral 237 denotes two views of the flow cross section which is kept free through the height difference between dent base 281 and film 3.

The marginal or edge-sided humps 229a and edges or angles 282 (see FIG. 11) of the spring element 227a are deliberately designed flatter or lower than the middle humps 229m (see FIG. 11) in the embodiment of FIGS. 8 and 9. The humps 229a and 229m form with regard to the direction of the valve base a slightly dented silhouette of about 1-4 times of the film thickness (see FIG. 11). In doing so, it is ensured that the humps 229a, 229m at the spring element 227a, 227b are capable on the one hand to raise the film 3 sufficiently away from the valve base without being on the other hand too strongly obstructed by its side gluing or welding seams. Thus, the limitedly hard film 3 is lifted such that it forms to a dent pointing to the outside (with regard to the cassette 1000) under the force of the spring element 227a, 227b. In this way, it releases the desired flow cross section through the flattened valve base or sealing seat-bar 226. The embodiment with flattened valve base or sealing seat-bar 226 and humps 229a, 229m which are elastically positioned on the spring element 227a, 227b (therefore flexible) and bent (i.e. with different heights, whereby the highest humps 229m are the ones in the middle) is particularly advantageous, as it does not cause any assembling or installation tolerance problems in both spatial directions of the film level between cassette 1000 and blood treatment apparatus 5000 (see FIG. 11).

Figure 10:
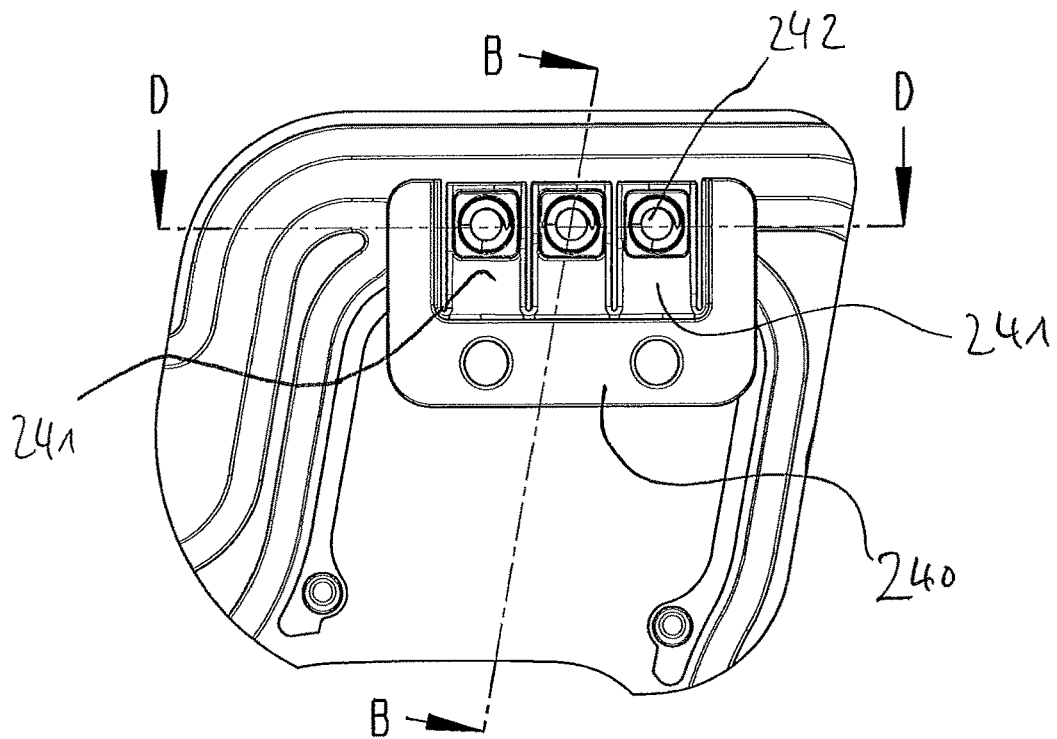
FIG. 10 shows in top view an embodiment of a blood treatment cassette inserted in and pressed by a blood treatment apparatus.
Figure 11:
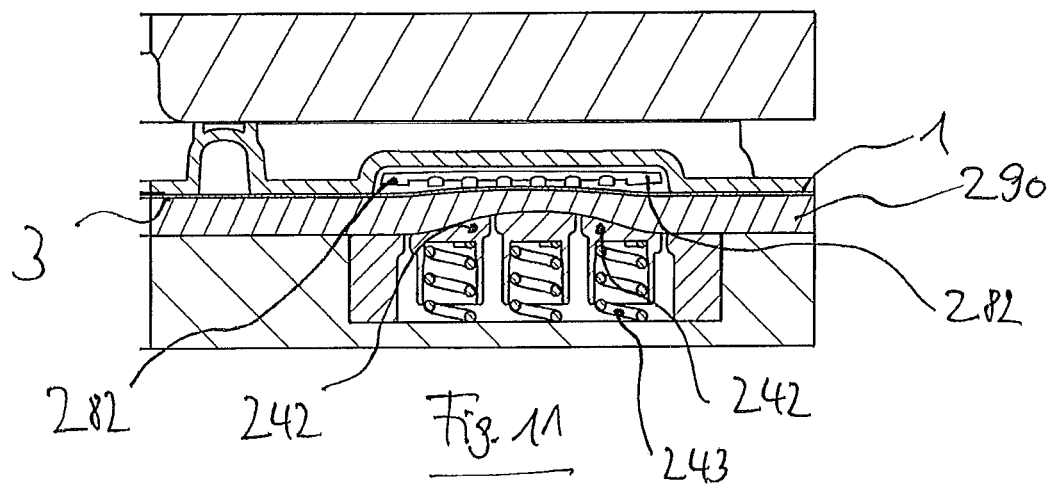
FIG. 11 shows in sectional view an embodiment of a blood treatment cassette inserted in and pressed by a blood treatment apparatus along the line D-D of FIG. 10.
Figure 12:
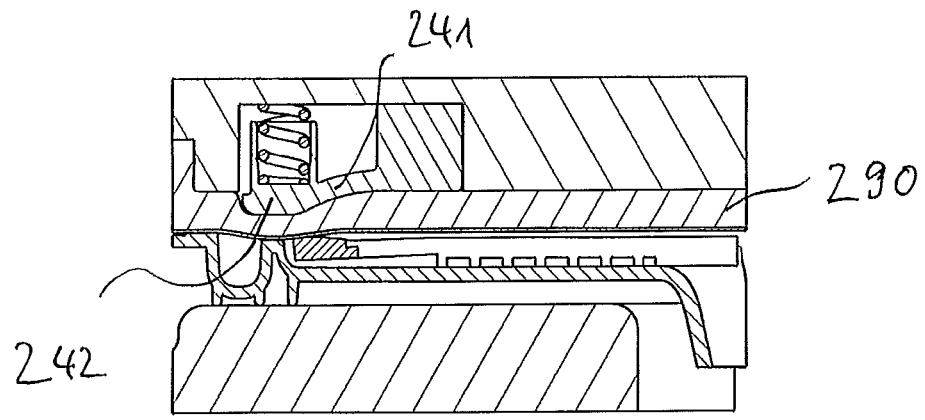
FIG. 12 shows in sectional view an embodiment of a blood treatment cassette inserted in and pressed by a blood treatment apparatus along the line B-B of FIG. 10.

FIG. 10 to FIG. 12 show an embodiment of a cassette 1000 inserted in the blood treatment apparatus and pressed by the latter, i.e. in an equipped state, in a top view (FIG. 10) and in sectional views along the line D-D of FIG. 10 (in FIG. 11) or line B-B (in FIG. 12), each with horizontally arranged film level.

In FIG. 10 one can see from the blood treatment apparatus only a pressure stamp 240 as part of an actuator-sensor-plate 290. The pressure stamp 240 is an example of an actuator. In this exemplary embodiment, the pressure stamp 240 is divided in laminated stamp 242 (part-actuators), see FIGS. 11 and 12, which are attached to the base body or core of the pressure stamp 240.

Thereby, an assembling tolerance balance or compensation results between cassette 1000 and blood treatment apparatus. Further, the valve sealing press force spreads durably and evenly on the entire valve base during use. For generating a relaxation-free force, exemplary spiral springs 243 made of spring steel which are easily inserted in and biased by a pocket or slot of the actuator-sensor-plate 290 during the assembling of the pressure stamp 240 are here provided. The complete pressure stamp 240 may be produced at low cost from unreinforced or fiber-reinforced thermoplastics in open/close injection molding tools.

It should be noted that the valve base or the valve-sealing seat-bar of the section 226 does not necessarily have to be dented. A straight course of the valve base is also encompassed by the present invention.

List of Reference Numerals

| Reference Numeral | Description |
| --- | --- |
| 1000 | cassette |
| 1 | hard part |
| 3 | film |
| 4 | sealing bar |
| 5 | closed or peripheral weld |
| 9 | arterial pressure measurement chamber |
| 11 | connector for the exit of blood from cassette 1000 |
| 13 | connector for the entry of blood into cassette 1000 |
| 15 | chamber with arterial post-pump, or pre-filter, pressure measureent site |
| 17 | arterial filter conduit |
| 19 | venous filter conduit |
| 21 | venous blood chamber |
| 23 | upper space of the venous blood chamber 21 |
| 25 | lower space of the venous blood chamber 21 |
| 27 | cross-sectional restriction of the hard part 1 |
| 29 | clot trap |
| 31 | venous patient connection |
| 33 | arterial heparin addition site |
| 35 | check valve of arterial addition site 33 |
| 36 | arterial heparin addition valve (phantom valve) |
| 37 | venous heparin addition site |
| 39 | check valve of the venous heparin addition site |
| 40 | venous heparin addition site (phantom valve) |
| 41 | substitute addition valve |
| 43 | connector for exit of substitute from the cassette 1000 |
| 45 | connector 45 for entry of substitute into the cassette 1000 |
| 47 | check valve for addition of substitute |
| 49 | substitute conduit |
| 51 | pre-dilution addition valve (phantom valve) |
| 53 | post-dilution addition valve (phantom valve) |
| 55 | single-needle sterile membrane |
| 57 | single-needle chamber |
| 59 | blood surge redirection element |
| 61 | single-needle blood valve (phantom valve) |
| 63 | evacuation site for vacuum coupling |
| 65 | primary alignment center |
| 67 | secondary alignment site |
| 69 | sealing bar |
| 71 | single-needle air connector |
| 73 | support bars having a height of 5 mm |
| 75 | support bars having a height of 8 mm |
| 77 | support bars having a height of 13 mm |
| 79 | support bars having a height of 24 mm |
| 81 | support bars having a height of 31 mm |
| 87 | blood pump |
| 89 | substituate pump |
| 90 | pump tube segment of substituate pump 89 |
| 93 | venous portion of extracorporeal circuit 3000 |
| 103 | venuos needle |
| 105 | blood inlet at the dialyzing device 2000 |
| 107 | blood outlet from the dialyzing device 2000 |
| 109 | single-needle access to patient 4000 |
| 201 | channels |
| 202 | chamber |
| 204 | closed, flat channel edge bars |
| 226 | section or film sealing seat-bar or valve seat or valve base |
| 227a, 227b | spring element or disposable spring element |
| 228 | spring clamp |
| 228a | spring arm or cantilever |
| 229a, 229m | humps |
| 230 | drainage groove |
| 231 | fixing pin |
| 232 | fixing bores |
| 233 | support humps |
| 234 | support ribs |
| 235 | split |
| 237 | height difference or flow cross section |
| 240 | Actuator; pressure stamp |
| 241 | actuator, bending joints |
| 242 | part-actuator; part-pressure stamp |
| 243 | spiral spring |
| 280 | hydrophobic membrane-support grid |
| 281 | dent base |
| 282 | Angles or edges |
| 288 | phantom or film valve |
| 290 | actuator-sensor-plate |

The invention claimed is:

1. A blood treatment cassette having a cassette body comprising a hard part and a film, wherein the film is connected to the hard part and at least partially covers the hard part,
wherein the hard part comprises a valve base that cooperates with a section of the film adjacent the valve base to form a valve, wherein the valve is configured to be moved from a first open position in which the valve base and the section of the film adjacent the valve base do not touch each other to a second position in which the valve base and the section of the film adjacent the valve base touch each other when a force is applied to the section of the film adjacent the valve base,
wherein the blood treatment cassette comprises a spring element connected to the hard part, the spring element comprising at least two humps defining at least one groove or recess therebetween, the spring element being configured such that each of the at least two humps contacts and applies force to the section of the film adjacent the valve base when the valve is in the first open position.

2. The blood treatment cassette according to claim 1, wherein the spring element is spring-loaded.

3. The blood treatment cassette according to claim 1, wherein the spring element is elastic.

4. The blood treatment cassette according to claim 1, wherein the valve is configured to be moved from the first position into the second position by pressure applied on the valve by an actuator of a blood treatment apparatus to which the blood treatment cassette is connected.

5. The blood treatment cassette according to claim 1, wherein the valve is a film valve or phantom valve.

6. The blood treatment cassette according to claim 1, wherein the humps are integral elements of the spring element connected to the hard part.

7. The blood treatment cassette according to claim 6, wherein the spring element comprises a functional element.

8. The blood treatment cassette according to claim 7, wherein the functional element comprises one or more of a hydrophobic-membrane support-grid, a clot trap pad or a check valve.

9. The blood treatment cassette according to claim 7, wherein a gap is formed between the spring element and the functional element.

10. The blood treatment cassette according to claim 9, wherein the gap is in the form of a split or a groove.

11. The blood treatment cassette according to claim 1, wherein the valve base defines a recess having a depth that is 1 to 3 times the thickness of the film.

12. The blood treatment cassette according to claim 1, wherein the valve base behind an adjacent channel edge bar is recessed to about 1 to 3 times the thickness of the film, in the direction toward an interior of the cassette.

13. The blood treatment cassette according to claim 1, wherein the spring element comprises a recessed upper edge whose curve rises relative to the valve base a distance of 1 to 4 times the thickness of the film.

14. A system comprising:
- a blood treatment apparatus comprising an actuator-sensor-plate; and
- a blood treatment cassette configured to be connected to the blood treatment apparatus, the blood treatment cassette having a cassette body comprising a hard part and a film, wherein the film is connected to the hard part and at least partially covers the hard part,
- wherein the hard part of the blood treatment cassette comprises a valve base that cooperates with a section of the film adjacent the valve base to form a valve, and the valve is configured to be moved from a first open position in which the valve base and the section of the film adjacent the valve base do not touch each other to a second position in which the valve base and the section of the film adjacent the valve base touch each other when a force is applied to the section of the film adjacent the valve base,
- wherein the blood treatment cassette comprises a spacer supported by the hard part,
- wherein the spacer is configured to apply, in the first position of the valve, force to the section of the film adjacent the valve base, and
- wherein the actuator-sensor-plate of the blood treatment apparatus comprises at least one actuator having at least two part-actuators configured to apply force to the section of the film adjacent the valve seat independently from each other.

15. The system according to claim 14, wherein the actuator-sensor-plate of the blood treatment apparatus comprises three or more part-actuators.

16. The blood treatment cassette according to claim 1, wherein the at least one groove or recess defined between the at least two humps is configured to permit drainage of fluid between the spring element and the film when the at least two humps are in contact with the film.

17. The blood treatment cassette according to claim 1, wherein the at least two humps extend from a substantially planar surface of the spring element.

* * * * *